United States Patent [19]

Klauke et al.

[11] 3,932,473

[45] Jan. 13, 1976

[54] PROCESS FOR THE MANUFACTURE OF 1-NITRO-ANTHRAQUINONE

[75] Inventors: Erich Klauke, Odenthal-Hahnenberg; Reinhold Schmitz, Blecher; Hans-Samuel Bien, Burscheid, all of Germany

[73] Assignee: Bayer Aktiengesellschaft, Leverkusen-Bayerwerk, Germany

[22] Filed: Apr. 20, 1973

[21] Appl. No.: 353,001

[30] Foreign Application Priority Data

Apr. 20, 1972 Germany.......................... 2219216

[52] U.S. Cl. .............................................. 260/369
[51] Int. Cl.² ......................................... C07C 79/37
[58] Field of Search ................................... 260/369

[56] References Cited
UNITED STATES PATENTS
3,417,146  12/1968  Linn et al. ......................... 260/609

FOREIGN PATENTS OR APPLICATIONS
46,428  10/1962  Poland .............................. 260/369
52,206  1/1967  Poland

OTHER PUBLICATIONS

Simons et al., Jacs 63, pp. 608–609, (1941).

Dokunichin et al., Z. vses. Chim. Obsc. 11,35 (1966) (cited by applicant).

*Primary Examiner*—Lorraine A. Weinberger
*Assistant Examiner*—Jane S. Myers
*Attorney, Agent, or Firm*—Plumley & Tyner

[57] ABSTRACT

Pure 1-nitro-anthraquinone is produced by nitrating anthraquinone in aqueous hydrogen fluoride containing about 5 – 30 weight percent of water with nitric acid as nitrating agent at about 0° – 150°C preferably 20° – 70°C.

4 Claims, No Drawings

PROCESS FOR THE MANUFACTURE OF 1-NITRO-ANTHRAQUINONE

Anthraquinine has already been nitrated in sulphuric acid[1], phosphoric acid[2], pure nitric acid[3] and finally also in anhydrous hydrofluoric acid[4], with suitable nitrating reagents, to give 1-nitro-anthraquinone. In all these media, in contrast to the statements in the literature, 2-nitroanthraquinone and dinitro-anthraquinone are also produced alongside the desired 1-nitro-anthraquinone, in particular also in nitric acid and anhydrous hydrogen fluoride[5].

1. C. Liebermann, Chemische Berichte 16, page 54 (1883)
2. German Offenlegungsschrift (German Published Specification) No. 2,103,360
3. U.S. Pat. No. 2,874,168
4. Polish Patent Specification No. 46,428
5. N. S. Dokunichin and Z. Z. Moiseeva, Z. vses. chim, Obsc. 11, 35 (1966); compare also Houben-Weyl, Methoden der organischen Chemie (Methods of Organic Chemistry) volume 10/1, 614 (1971)

It has now been found that a substantially purer 1-nitro-anthraquinone than that obtained according to the processes previously known is obtained if the nitration is carried out in aqueous hydrogen fluoride. Here, admittedly, approx. 10–13 percent of 2-nitro-anthraquinone are also produced as a by-product, as in the case of the nitrations in other media, but the further nitration of the initially produced 1-nitro-anthraquinone is largely avoided.

The nitration is advantageously carried out in hydrogen fluoride containing 5–30, preferably 10–25, percent by weight of water, and using a customary nitrating agent. Examples of possible nitrating agents are: nitric acid, salts of nitric acid such as $KNO_3$, $Cu(NO_3)_2$, $NaNO_3$, $Co(NO_3)_2$, $N_2O_5$, $N_2O_4$, esters of nitric acid such as $CH_3-CH_2-O-NO_3$, glycerine trinitrate, $CH_3-O-NO_3$) and nitronium salts such as $NO_2BF_4$. The preferred nitrating agent is nitric acid. Here, it is technically particularly advantageous that it is not necessary to start from the 95–100 percent strength acid which is difficult to handle, but that the 68 percent strength $HNO_3$ can be used, its water content serving to dilute the hydrogen fluoride. The nitrating agent is employed in the theoretical amount or in an excess of 20–200 percent, with the requisite excess depending on the remaining reaction conditions. The reaction temperature is between 0°C and 150°C, preferably between 20°C and 70°C.

Under the conditions indicated above, the anthraquinone can be used in rather high concentrations for the nitration, but the method of nitrating 2 to 0.3 parts of anthraquinone in 1 part of hydrogen fluoride has proved particularly successful.

The duration of nitration depends on the remaining experimental conditions and varies between about 1 hour and 10 hours.

In general, the nitric acid, mixed with the hydrogen fluoride, is added to a suspension of the anthraquinone in hydrogen fluoride, for example 85 percent strength hydrogen fluoride, in general over the course of about 5–30 minutes, and the mixture is subsequently heated to refluxing (approx. 53°C). Of course, the nitric acid can be added, without prior dilution with hydrogen fluoride, to the suspension of anthraquinone in hydrogen fluoride.

A possible procedure is also to introduce simultaneously identical molar amounts of anthraquinone (dissolved in 100 percent strength hydrogen fluoride) and a nitration mixture consisting of nitric acid, hydrogen fluoride and water from separate containers into the heated reaction kettle over the course of about 1–5 hours. This avoids a major excess of nitric acid in the reaction kettle. At the same time the reaction can be conducted in such a way that during the entire reaction time an approximately constant acid concentration is maintained.

It was surprising, and not foreseeable from the state of the art, that under the abovementioned conditions the anthraquinone can be nitrated practically completely (residual anthraquinone content <0.5 percent) and that the resulting 1-nitro-anthraquinone largely avoids a further nitration (combined content of 1.5- and 1,8-dinitro-anthraquinone in the nitration mixture approx. 6 percent).

The isolation of the 1-nitro-anthraquinone can be effected in the usual manner by pouring the reaction mixture out into water.

The isolation can also be effected by filtering the batch, after completion of the reaction, through a filter press or separating off the mother liquor in a centrifuge and subsequently washing the solid residue with water and drying it.

It is however also possible to evaporate off the hydrofluoric acid, together with the excess of the nitric acid, in a suitable manner after completion of the reaction and thus to recover a solution of nitric acid in hydrofluoric acid which can again be employed in the reaction. Accordingly, in this process no waste acids would arise and contamination of the effluent and to the flue gases would largely be excluded.

The 1-nitro-anthraquinone manufactured in this way can be reduced directly, in a known manner, to 1-amino-anthraquinone, for example by treatment with an aqueous solution of sodium sulphide. It can however also — if particular standards of purity are required — be further purified according to known processes, for example by treating the crude 1-nitro-anthraquinone with acid amides according to German Offenlegungsschrift (German Published Specification) No. 2,039,822, halogenated alkanes according to German Offenlegungsschrift (German Published Specification) No. 2,142,100, or aqueous solutions of sodium sulphite according to U.S. Pat. No. 2,302,729, and also by recrystallisation from suitable solvents, for example from glacial acetic acid, and finally also by distillation according to German Patent Specification No. 281,490.

EXAMPLE 1

50 g of anthraquinone are suspended in 50 ml of hydrogen fluoride (85% strength). A mixture of 16 ml of $HNO_3$ (98% strength) and 50 ml of hydrogen fluoride (85% strength) is added dropwise over the course of ½ hour, the reaction mixture is then heated for 4 hours to refluxing (53°C) and diluted with 1 liter of water, and the product is filtered off, washed until neutral and dried. 60.5 g of nitroanthraquinone of the following composition are obtained:

80.1% of 1-nitro-anthraquinone
2.3% of 1,5-dinitro-anthraquinone
2.3% of 1,8-dinitro-anthraquinone
2-3% of anthraquinone
approx. 5% of 2-nitro-anthraquinone
(remainder: 1.6- + 1,7-dinitro-anthraquinone).

EXAMPLES 2 – 5

50 g of anthraquinone are suspended in 50 ml of hydrogen fluoride of the concentration indicated in Table 1. A mixture of 16 ml of HNO$_3$ (98% strength) and 50 ml of hydrogen fluoride of the concentration indicated in Table 1 is added dropwise over the course of ½ hour and the batch is then heated to refluxing temperature for 8 hours and worked up as in Example 1. The yield and quality of the nitro-anthraquinone obtained are shown in Table 1.

Table 1

| Example | Concentration of HF | Crude yield g | 1-nitro-anthraquinone % | 1,5-dinitro-anthraquinone % | Analysis of the crude product 1,8-dinitro-anthraquinone % | anthra-quinone % | 2-nitro-anthraquinone % |
|---|---|---|---|---|---|---|---|
| 2 | 80% | 59.8 | 58.1 | 1.3 | 1.2 | >20 | 2–3 |
| 3 | 85% | 60.8 | 79.3 | 2.9 | 3.1 | 0.5–1 | approx. 5 |
| 4 | 90% | 61.3 | 67.4 | 9.7 | 9.4 | 0.25 | 0.25 |
| 5 | 95% | 61.3 | 60.3 | 11.1 | 12.5 | 0.5 | 0.5 |

EXAMPLE 6

500 g of anthraquinone and 500 ml of 85 percent strength hydrogen fluoride are initially introduced into a 4 liter Venuleth vessel and stirred for 15 minutes. A mixture of 500 ml of hydrogen fluoride (85 percent strength) and 140 ml of nitric acid (98 percent strength) is added at room temperature over the course of 5 minutes. The bath temperature of the Venuleth vessel is then raised to 50°C and the mixture is stirred at this temperature for 8 hours. The hydrogen fluoride is largely stripped off in vacuo (approx. 50 mm Hg) at the same temperature. The residue is treated with water, filtered off, washed and dried. 610 g of nitro-anthraquinone of the following composition are obtained:

78.5% of 1-nitro-anthraquinone
3.7% of 1,5-dinitro-anthraquinone
4.5% of 1,8-dinitro-anthraquinone
<0.5% – 1% of anthraquinone
approx. 3% of 2-nitro-anthraquinone

EXAMPLE 7

1,000 g of anthraquinone and 500 ml of hydrogen fluoride (90 percent strength) are initially introduced into a 4 liter Venuleth vessel and stirred for 15 minutes. A mixture of 500 ml of hydrogen fluoride (90 percent strength) and 240 ml of nitric acid (98 percent strength) is added at room temperature over the course of 5 minutes. The bath temperature of the Venuleth vessel is then raised to 50°C and the mixture is stirred at this temperature for 4 hours. Working up takes place as in Example 6. 1,200 g of nitro-anthraquinone of the following composition are obtained:

79.1% of 1-nitro-anthraquinone
1.6% of 1,5-dinitro-anthraquinone
2.1% of 1,8-dinitro-anthraquinone
approx. 5% of anthraquinone
approx. 7% of 2-nitro-anthraquinone

EXAMPLE 8

100 g of anthraquinone are suspended in 200 g of hydrofluoric acid (85 percent strength); 24 ml of HNO$_3$ (98 percent strength) are added at a temperature of approx. 10°C and the mixture is heated to about 50°C whilst stirring. The reaction is allowed to take place for 4 hours at a constant bath temperature of 50°C. Thereafter the batch is cooled to 5° – 10°C and filtered on a filter press. The press cake, having a residual moisture content of approx. 30% is washed with water until neutral and dried (=A). The expressed mother liquor is left to stand overnight. Hereupon, some crystals precipitate, which are filtered off. (''B). Thereafter, a sample of the mother liquor is added to ice water in order to determine the dissolved organic component. The crystals which precipitate are filtered off (=C).

Analyses:

| | 1-nitro-anthra-quinone | anthra-quinone | 2-nitro-anthra-quinone | 1,5-dinitro-anthraquin-one | 1,8-di-nitro-anthra-quinone |
|---|---|---|---|---|---|
| A | 82% | 1 – 2% | 3 – 4% | 3.2% | 3.1% |
| B | 60.6% | 2 – 3% | 10% | 2.2% | 2.6% |
| C | 10.7% | main product | not determined | 0.25% | 0.81% |

The total amount of the organic component is 2.4 percent.

EXAMPLE 9

50 g of anthraquinone are suspended in 100 g of 85 percent strength HF in the originally introduced batch and the bath temperature of the reaction kettle is set to 50°C. The solutions A and B are now run in dropwise, uniformly and simultaneously, from two dropping funnels over the course of 2 hours.

Solution A: 450 g of anthraquinone in 350 g of 100 percent strength HF
Solution B: 415 g of 100 percent strength HF, 119 g of 98 percent strength HNO$_3$ and 135 g of H$_2$O.

After completion of the addition, the reaction is allowed to continue for 4 hours, the total batch is added to ice and the product is washed until neutral and dried.
Analysis 79.8% of 1-nitro-anthraquinone, 2% of anthraquinone and 8.9% of 2-nitro-anthraquinone
2 % of 1,6-dinitro-anthraquinone
2.8% of 1,7-dinitro-anthraquinone
2.4% of 1,5-dinitro-anthraquinone
2.0% of 1,8-dinitro-anthraquinone

We claim:
1. Process for the manufacture of 1-nitro-anthraquinone by reacting anthraquinone and a nitrating agent for anthraquinone in aqueous hydrogen fluoride containing 5–30 percent water by weight at a temperature between 0°C and 150°C.

2. Process according to claim 1, characterised in that the nitration is carried out in hydrogen fluoride containing 10–25 percent by weight, of water.

3. Process according to claim 1, characterised in that nitric acid is used as the nitrating agent.

4. Process according to claim 1, characterised in that the nitration is carried out between 20°C and 70°C.

* * * * *